United States Patent
Ono et al.

(10) Patent No.: US 9,097,248 B2
(45) Date of Patent: Aug. 4, 2015

(54) PULSATING FLOW GENERATING APPARATUS AND METHOD OF CONTROLLING PULSATING FLOW GENERATING APPARATUS

(75) Inventors: Yasuhiro Ono, Matsumoto (JP); Shigeo Sugimura, Okaya (JP); Hideki Kojima, Matsumoto (JP)

(73) Assignee: SEIKO EPSON CORPORATION, Tokyo (JP)

( * ) Notice: Subject to any disclaimer, the term of this patent is extended or adjusted under 35 U.S.C. 154(b) by 1013 days.

(21) Appl. No.: 12/833,115

(22) Filed: Jul. 9, 2010

(65) Prior Publication Data

US 2011/0006127 A1    Jan. 13, 2011

(30) Foreign Application Priority Data

Jul. 10, 2009    (JP) ................. 2009-163388

(51) Int. Cl.
| | |
|---|---|
| B05B 1/08 | (2006.01) |
| F04B 43/09 | (2006.01) |
| B05B 17/06 | (2006.01) |
| F04B 43/04 | (2006.01) |
| A61B 17/3203 | (2006.01) |
| A61B 17/00 | (2006.01) |

(52) U.S. Cl.
CPC .......... *F04B 43/095* (2013.01); *A61B 17/3203* (2013.01); *B05B 17/0607* (2013.01); *F04B 43/046* (2013.01); *A61B 2017/00154* (2013.01)

(58) Field of Classification Search
CPC .... F04B 43/095; F04B 45/047; F04B 43/046; B05B 17/0607; A61B 17/3203; A61B 2017/00154

USPC .............. 239/102.2, 124, 68; 417/370, 413.2
See application file for complete search history.

(56) References Cited

U.S. PATENT DOCUMENTS

| | | | |
|---|---|---|---|
| 7,011,507 B2 * | 3/2006 | Seto et al. ................... | 417/412 |
| 7,302,970 B2 | 12/2007 | Sugioka et al. | |
| 2005/0019180 A1 | 1/2005 | Seto et al. | |
| 2008/0086077 A1 | 4/2008 | Seto et al. | |
| 2010/0021319 A1 | 1/2010 | Seto et al. | |
| 2010/0046681 A1 | 2/2010 | van Nee | |

FOREIGN PATENT DOCUMENTS

| | | |
|---|---|---|
| JP | 2004-125172 | 4/2004 |
| JP | 2005-133704 | 5/2005 |
| JP | 2006-316785 | 11/2006 |
| JP | 2008-082202 | 4/2008 |
| JP | 2010-075589 | 4/2010 |
| JP | 2010-084564 A | 4/2010 |

* cited by examiner

*Primary Examiner* — Jason Boeckmann
(74) *Attorney, Agent, or Firm* — Maschoff Brennan (57) ABSTRACT

Pulsating flow generating apparatus that changes the volume of a fluid chamber and injects fluid from a fluid injection opening in a pulsed manner, includes: an inlet flow channel for supplying fluid from a fluid supplying unit to the fluid chamber; a volume changing unit that changes the volume of the fluid chamber; an outlet flow channel that delivers the fluid from the fluid chamber to the fluid injection opening; a discharge flow channel that discharges the fluid from the fluid chamber; and an opening and closing valve that opens and closes the discharge flow channel, wherein the synthetic inertance of the discharge flow channel is set smaller than the synthetic inertance of the outlet flow channel, an operation of the volume changing unit is started while closing the opening and closing valve, and the operation of the volume changing unit is stopped while opening the opening and closing valve.

3 Claims, 5 Drawing Sheets

FIG. 9

PULSATING FLOW GENERATING APPARATUS AND METHOD OF CONTROLLING PULSATING FLOW GENERATING APPARATUS The entire disclosure of Japanese Patent Application No. 2009-163388, filed Jul. 10, 2009 is expressly incorporated by reference herein.

BACKGROUND

1. Technical Field

The present invention relates to a pulsating flow generating apparatus configured to inject fluid in a pulsed manner, and a method of controlling the pulsating flow generating apparatus.

2. Related art

In the related art, a technology for cutting or ablating an object by injecting fluid in a pulsed manner is known. For example, in a medical field, as a fluid injecting apparatus to be used as a surgical instrument for cutting or ablating anatomy, the one having a fluid chamber whose volume is changed by an operation of a volume changing unit and a nozzle communicated with the fluid chamber, and being configured to supply the fluid into the fluid chamber and operate the volume changing unit, thereby converting the fluid into a pulsating flow and injecting the fluid at a highspeed in a pulsed manner from a nozzle is proposed (see JP-A-2008-082202, for example).

JP-A-2008-082202 is an example of the related art.

According to JP-A-2008-082202, the fluid is supplied to the fluid chamber by a pump as a fluid supplying unit. However, there is a case where the fluid supplied to the fluid chamber flows out from the nozzle before reaching a flow rate or a pressure required for incising or ablating the anatomy. If the fluid flows out from the nozzle before reaching the flow rate or the pressure required for incising or ablating the anatomy, the visibility of a field of operation at a portion to be incised or ablated is exacerbated by such the fluid, which causes lowering of the efficiency and safety of the operation.

SUMMARY

An advantage of some aspects of the invention is to solve at least a part of the problems mentioned above and can be embodied as the following embodiments or application examples.

APPLICATION EXAMPLE 1

Application Example 1 is directed to a pulsating flow generating apparatus that changes the volume of a fluid chamber and injects fluid from a fluid injection opening in a pulsed manner including: an inlet flow channel for supplying fluid from a fluid supplying unit to the fluid chamber; a volume changing unit that changes the volume of the fluid chamber; an outlet flow channel that delivers the fluid from the fluid chamber to the fluid injection opening; a discharge flow channel that discharges the fluid from the fluid chamber; and an opening and closing valve that opens and closes the discharge flow channel, wherein the synthetic inertance of the discharge flow channel is set to be smaller than the synthetic inertance of the outlet flow channel, and an operation of the volume changing unit is started while closing the opening and closing valve, and the operation of the volume changing unit is stopped while opening the opening and closing valve.

According to Application Example 1, the operation of the volume changing unit is stopped while opening the opening and closing valve. In this case, since the synthetic inertance of the discharge flow channel is set to be smaller than the synthetic inertance of the outlet flow channel, the fluid in the fluid chamber is apt to flow toward the discharge flow channel rather than toward the outlet flow channel. Therefore, in the state in which the operation of the volume changing unit is stopped, the unnecessary fluid is restrained from flowing out from the fluid injection opening, so that the visibility of the field of operation at the portion to be incised or ablated is enhanced.

APPLICATION EXAMPLE 2

Application Example 2 is directed to the pulsating flow generating apparatus of the foregoing application example, wherein the operation of the volume changing unit is started after a time lag from the closing of the opening and closing valve, and the operation of the volume changing unit is stopped after a time lag from the opening of the opening and closing valve.

According to Application Example 2, the operation of the volume changing unit is started in the state in which the opening and closing valve is closed. Therefore, the pressure in the fluid chamber is sufficiently increased by the operation of the volume changing unit, so that liquid can be injected at a high speed in a pulsed manner.

According to Application Example 2, the operation of the volume changing unit is stopped in the state in which the opening and closing valve is opened. Since the fluid flows to the discharge flow channel and is discharged therefrom irrespective of the operation of the volume changing unit by opening the opening and closing valve preferentially, the fluid is restrained from flowing out from the fluid opening, so that the visibility of the field of operation at the portion to be incised or ablated is enhanced.

APPLICATION EXAMPLE 3

Application Example 3 is directed to a pulsating flow generating apparatus that changes the volume of a fluid chamber and injects fluid from a fluid injection opening in a pulsed manner including: an inlet flow channel for supplying fluid from a fluid supplying unit to the fluid chamber; a volume changing unit that changes the volume of the fluid chamber; an outlet flow channel that delivers the fluid from the fluid chamber to the fluid injection opening; a discharge flow channel that discharges the fluid from the fluid chamber; an opening and closing valve that opens and closes the discharge flow channel; and a sucking unit disposed on the downstream side of the opening and closing valve where the fluid is discharged for sucking the fluid, wherein an operation of the sucking unit is stopped and an operation of the volume changing unit is started while closing the opening and closing valve, and the operation of the sucking unit is started and the operation of the volume changing unit is stopped while opening the opening and closing valve.

According to Application Example 3, since the opening and closing valve is opened when stopping the operation of the volume changing unit and starting the operation of the sucking unit, thereby forcedly discharging the fluid in the fluid chamber, the same advantages as in Application Example 1 described above are achieved.

Also, by the provision of the sucking unit, setting of the magnitude relation of the synthetic inertance of the discharge flow channel and the synthetic inertance of the outlet flow channel is no longer necessary, so that the constraint in terms of designs of the inlet flow channel and the outlet flow channel of the pulsating flow generating apparatus may be eliminated.

APPLICATION EXAMPLE 4

Application Example 4 is directed to the foregoing pulsating flow generating apparatus, which is preferably configured in such a manner that the operation of the volume changing unit is started after a time lag from the closing of the opening and closing valve and the stopping of the operation of the sucking unit; and the operation of the volume changing unit is stopped after a time lag from the opening of the opening and closing valve and the starting of the operation of the sucking unit.

According to Application Example 4, the operation of the volume changing unit is started after a time lag from the closing of the opening and closing valve and the stopping of the operation of the sucking unit; and the operation of the volume changing unit is stopped after a time lag from the opening of the opening and closing valve and the starting of the operation of the sucking unit. Therefore, the same advantages as Application Example 2 described above are achieved.

APPLICATION EXAMPLE 5

Application Example 5 is directed to the pulsating flow generating apparatus, wherein the discharge flow channel is communicated with the outlet flow channel.

The fluid to be flowed out from the fluid chamber can be discharged either by bringing the discharge flow channel into communication with the fluid chamber or bringing the same with the outlet flow channel. However, in Application Example 3, the discharge flow channel is configured to be communicated with the outlet flow channel. In this configuration, a connecting portion between the fluid chamber and the flow channel communicated directly with the fluid chamber can be eliminated, so that air bubbles to be built up in the connecting portion may be reduced. The pulsating flow generating apparatus configured to generate a pulsating flow by changing the volume of the fluid chamber with the volume changing unit may not be able to generate the pulsating flow sufficient for incising or ablating the anatomy if the air bubbles exist in the fluid chamber because the internal pressure cannot be increased sufficiently. Therefore, with the structure in which the discharge flow channel is brought into communication with the outlet flow channel, air bubbles are restrained from building up in the fluid chamber, and the pressure in the fluid chamber may be increased to a desired pressure.

APPLICATION EXAMPLE 6

Application Example 6 is directed to a method of controlling a pulsating flow generating apparatus that changes the volume of a fluid chamber and injects fluid from a fluid injection opening in a pulsed manner having an inlet flow channel for supplying fluid from a fluid supplying unit to the fluid chamber; a volume changing unit that changes the volume of the fluid chamber; an outlet flow channel that delivers the fluid from the fluid chamber to the fluid injection opening; a discharge flow channel that discharges the fluid from the fluid chamber; and an opening and closing valve that opens and closes the discharge flow channel, wherein the synthetic inertance of the discharge flow channel is set to be smaller than the synthetic inertance of the outlet flow channel, including: stopping the fluid supplying unit and the volume changing unit and operating the fluid supplying unit from a stopped state of the pulsating flow generating apparatus in which the opening and closing valve is opened; closing the opening and closing valve; operating the volume changing unit to cause the fluid to be injected from the fluid injection opening in a pulsed manner; and stopping at least the volume changing unit from a group of the fluid supplying unit and the volume changing unit while opening the opening and closing valve.

According to the method of controlling in Application Example 6, the first step of operating the fluid supplying unit, stopping the volume changing unit, and opening the opening and closing valve corresponds to a startup preparation period of the pulsating flow generating apparatus for starting the supply of the fluid into the fluid chamber. In this period, a state in which the fluid can be supplied to the fluid chamber with a predetermined flow rate per unit time is achieved. In this period, since the opening and closing valve is opened, the fluid is flowed to the discharge flow channel, and the fluid is prevented from flowing out from the fluid injection opening, so that the visibility of the field of operation at the portion to be incised or ablated is enhanced.

The second step is a startup period of the pulsating flow generating apparatus for closing the opening and closing valve while operating the fluid supplying unit. In this period, the opening and closing valve is closed before starting the operation of the volume changing unit, and the pressure in the fluid chamber is increased to a pressure required for injecting the fluid. Therefore, the fluid having energy sufficient for incising or ablating the anatomy can be injected in a pulsed manner at a high speed immediately after having started the operation of the volume changing unit.

The third step is a period for a stationary operation of the pulsating flow generating apparatus. In this period, the volume changing unit is operated in the state in which the opening and closing valve is closed, the pressure in the fluid chamber is sufficiently increased, and the fluid having energy sufficient for incising or ablating the anatomy can be injected in a pulsed manner at a high speed.

In the fourth step, the pulsating flow generating apparatus is stopped. In this case, by keeping the opening and closing valve opened in a case where there is the time difference from the stop of the operation of the fluid supplying unit to the actual stop of a supply of the fluid, the fluid is restrained from flowing out from the fluid injection opening, so that the visibility of the field of operation at the portion to be incised or ablated is enhanced.

The fourth step in Application Example 6 includes a temporary halt period for opening the opening and closing valve during the operation of the pulsating flow generating apparatus. Here, the temporary halt period means, for example, a period of stopping the pulsating flow generating apparatus during the operation temporarily and operating again.

In this method of controlling as described above, the opening and closing valve is opened when the pulsating flow generating apparatus is operated (a state in which the fluid supplying unit and the volume changing unit are operated and the opening and closing valve is closed). Since the synthetic inertance of the discharge flow channel is set to be smaller than the synthetic inertance of the outlet flow channel, the fluid flows out from the discharge flow channel even in a state in which the volume changing unit is operated, so that flowing out from the fluid injection opening is restrained, and the visibility of the field of operation at the portion to be incised or ablated is enhanced.

Since the fluid supplying unit is continuously operated in the temporary halt period, a restart of the operation is achieved by the transition from the temporary halt period to the second step, and to the third step in sequence, so that the time lag until the restart of the operation can be shortened.

APPLICATION EXAMPLE 7

Application Example 7 is directed to a method of controlling a pulsating flow generating apparatus that changes the volume of a fluid chamber and injects fluid from a fluid injection opening in a pulsed manner, having an inlet flow channel for supplying fluid from a fluid supplying unit to the fluid chamber, a volume changing unit that changes the volume of the fluid chamber, an outlet flow channel that delivers the fluid from the fluid chamber to the fluid injection opening, a discharge flow channel that discharges the fluid from the fluid chamber, an opening and closing valve that opens and closes the discharge flow channel, and a sucking unit disposed on the downstream side of the opening and closing valve where the fluid is discharged for sucking the fluid, including: stopping the fluid supplying unit, the volume changing unit, and the sucking unit, and operating the fluid supplying unit and the sucking unit from a stopped state of the pulsating flow generating apparatus in which the opening and closing valve is opened; closing the opening and closing valve and stopping the sucking unit; operating the volume changing unit to cause the fluid to be injected from the fluid injection opening in a pulsed manner; opening the opening and closing valve, stopping the volume changing unit, and stopping the fluid supplying unit or operating the fluid supplying unit and the sucking unit.

According to Application Example 7, since the opening and closing valve is opened and, simultaneously, the operation of the volume changing unit is stopped and the sucking unit is operated, thereby forcedly discharging the fluid in the fluid chamber, the same advantages as in Application Example 4 described above are achieved.

The fourth step in Application Example 7 includes a temporary halt period for opening the opening and closing valve and operating the sucking unit during the operation of the pulsating flow generating apparatus.

In this method of controlling as described above, the opening and closing valve is opened in a state in which the fluid supplying unit and the volume changing unit are operated. Since the sucking unit is disposed in the discharge flow channel, the fluid is forcedly sucked even in a state in which the volume changing unit is operated, and hence is restrained from flowing out from the fluid injection opening further reliably, so that the visibility of the field of operation at the portion to be incised or ablated is enhanced.

In addition, the restart of the operation is enabled by the transition from the temporary halt period to the second step and to the third step in sequence, so that the time lag until the restart of the operation can be shortened.

BRIEF DESCRIPTION OF THE DRAWINGS

The invention will be described with reference to the accompanying drawings, wherein like numbers reference like elements.

DESCRIPTION OF EXEMPLARY EMBODIMENTS

Referring now to the drawings, an embodiment of the invention will be described. A pulsating flow generating apparatus according to the invention maybe employed in various modes such as graphics-drawing using ink or the like, washing of minute substances or structures, surgical knives, and so on. In the embodiments shown below, a pulsating flow generating apparatus suitable for incising or ablating anatomy is exemplified for description. Therefore, fluid used in the embodiment is liquid such as water or physiologic saline. FIG. 2, FIG. 5, FIG. 8, and FIG. 9 described below are diagrammatic illustrations in which scale ratios of members or portions in vertical and lateral directions are different from actual ratios for the sake of convenience of illustration.

First Embodiment

Figure 1:
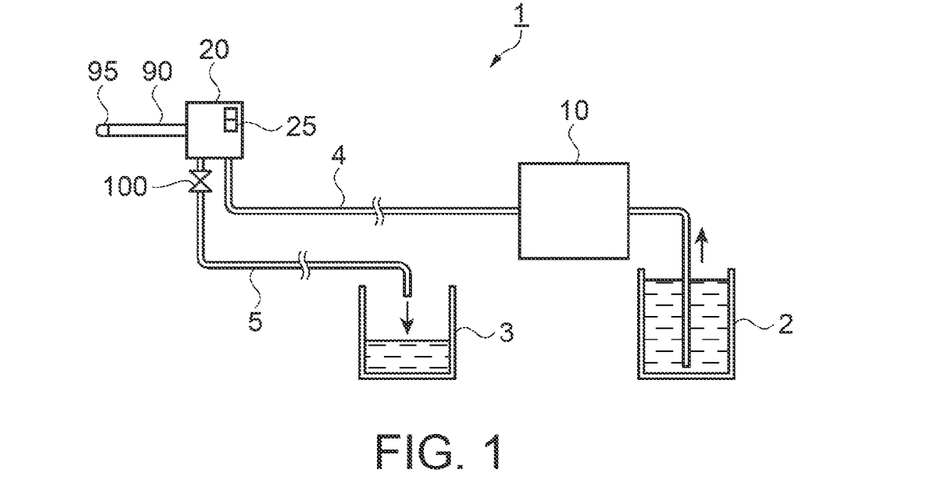
FIG. 1 is an explanatory drawing showing a configuration of a fluid injecting apparatus according to a first embodiment.

FIG. 1 is an explanatory drawing showing a configuration of a fluid injecting apparatus as a surgical instrument according to a first embodiment. In FIG. 1, a fluid injecting apparatus 1 includes a liquid supply container 2 configured to store liquid (hereinafter, referred to simply as container 2), a pump 10 as a fluid supplying unit, and a pulsating flow generating apparatus 20 configured to convert the liquid supplied from the pump 10 into a pulsating flow. The pump 10 and the pulsating flow generating apparatus 20 are connected by a liquid supply tube 4 (hereinafter, referred to simply as tube 4).

The pulsating flow generating apparatus 20 includes a thin pipe-shaped connecting flow channel tube 90 connected thereto, and a nozzle 95 reduced in flow channel diameter is fitted to a distal end portion of the connecting flow channel tube 90.

The pulsating flow generating apparatus 20 also includes a liquid discharge tube 5 (hereinafter, referred to simply as tube 5) connected thereto, and a terminal end thereof reaches a liquid discharging container 3 (hereinafter, referred to simply as container 3). Disposed near a connecting portion between the tube 5 and the pulsating flow generating apparatus 20 is an opening and closing valve 100 configured to open and close a flow channel of the tube 5.

A flow of the liquid in the fluid injecting apparatus 1 will be described in brief. The liquid stored in the container 2 is sucked by the pump 10, and is supplied to the pulsating flow generating apparatus 20 via the tube 4 at a constant pressure. The pulsating flow generating apparatus 20 includes a fluid chamber 80 (see FIG. 2) and a volume changing unit configured to change the volume of the fluid chamber 80, and is configured to operate the volume changing unit and generate a pulsating flow in the fluid chamber 80, and inject the liquid at a high speed in a pulsed manner via the connecting flow channel tube 90 and the nozzle 95.

The term "pulsating flow" here means a flow of the liquid constant in direction of flow and associated with regular or irregular changes in flow rate or flow velocity. The pulsating flow includes an intermittent flow including flow and stop of the liquid repeated alternately. However, what is essential is that the flow rate or the flow velocity of the liquid varies regularly or irregularly, so that it does not necessarily have to be the intermittent flow. Likewise, the term "injecting the liquid in a pulsed manner" means an injection of liquid in which the flow rate or the moving velocity of the liquid to be injected varies regularly or irregularly. As an example of the pulsed injection, an intermittent injection in which the injection and non-injection of the liquid are repeated is exemplified. However, what is essential for the flow rate or the moving velocity of the liquid to be injected is to vary regularly or irregularly, and hence it does not necessarily have to be the intermittent injection. The pulsating flow generating apparatus 20 will be described later with reference to FIG. 2.

The tube 5 is connected to a discharge flow channel 83 (see FIG. 2) which communicates with the fluid chamber 80. The opening and closing valve 100 is provided at the connecting portion between the discharge flow channel 83 and the tube 5, and liquid unnecessary to the incision or ablation of anatomy is discharged to the container 3.

When conducting a surgical operation using the fluid injecting apparatus 1, a portion held by a personal who conducts the surgical operation is the pulsating flow generating apparatus 20. Therefore, the tubes 4 and 5 are preferably flexible as much as possible.

Subsequently, the structure of the pulsating flow generating apparatus 20 according to the first embodiment will be described.

Figure 2:
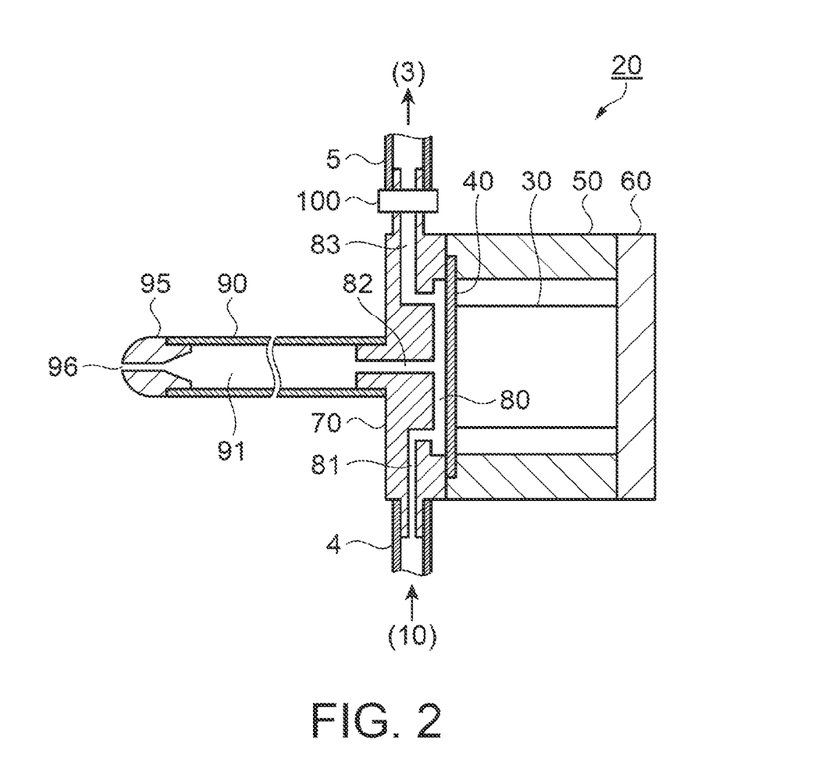
FIG. 2 is a cross-sectional view of a pulsating flow generating apparatus according to the first embodiment taken along the direction of injection of liquid.

FIG. 2 is a cross-sectional view of a pulsating flow generating apparatus according to the first embodiment taken along the direction of injection of the liquid.

The pulsating flow generating apparatus 20 includes an inlet flow channel 81 configured to supply liquid from the pump 10 to the fluid chamber 80 via the tube 4, a piezoelectric element 30 and a diaphragm 40 as the volume changing unit configured to change the volume of the fluid chamber 80, an outlet flow channel 82 configured to deliver the liquid from the fluid chamber 80 to a fluid injection opening 96, the discharge flow channel 83 configured to discharge the liquid outward from the fluid chamber 80, and the opening and closing valve 100 configured to open and close the discharge flow channel 83.

The diaphragm 40 is formed of a disk-shaped thin metal plate, and is in close contact between a lower case 50 and an upper case 70. The piezoelectric element 30 is a laminated piezoelectric element in the first embodiment, and one of both end portions is secured to the diaphragm 40, and the other one of those is secured to a bottom plate 60.

The fluid chamber 80 is a space defined by a depression formed on a surface of the upper case 70 opposing the diaphragm 40 and the diaphragm 40. Opened at a substantially center of the fluid chamber 80 is the outlet flow channel 82.

The upper case 70 and the lower case 50 are integrally joined at respective opposed surfaces thereof. The connecting flow channel tube 90 having a connecting flow channel 91 in communication with the outlet flow channel 82 is fitted on the upper case 70, and the nozzle 95 is inserted into the distal end portion of the connecting flow channel tube 90. The fluid injection opening 96 reduced in flow channel diameter is formed in the nozzle 95 so as to be opened therefrom. The connecting flow channel 91 constitutes part of the outlet flow channel 82.

The upper case 70 is formed with the inlet flow channel 81 and the discharge flow channel 83, which communicate with the fluid chamber 80, and the tube 4 is attached to the inlet flow channel 81. The tube 5 is attached to the discharge flow channel 83, and the opening and closing valve 100 is mounted to a joint portion between the discharge flow channel 83 and the tube 5. Although an electromagnetic valve, an air operated valve or the like may be employed as the opening and closing valve 100, the electromagnetic valve having a high response with respect to opening and closing operation signals is preferably used.

Referring now to FIG. 1 and FIG. 2, the fluid discharging operation of the pulsating flow generating apparatus 20 in the first embodiment will be described. Discharge of the fluid from the pulsating flow generating apparatus 20 in the first embodiment is performed by the difference between a synthetic inertance L1 on the side of the inlet flow channel 81 and a synthetic inertance L2 on the side of the outlet flow channel 82.

The inertance will be described first.

The inertance L is expressed by an expression $L = \rho \times h / S$, where $\rho$ is a density of the fluid, S is a cross-sectional area of the flow channel, and h is the length of the flow channel. By deforming a dynamic equation in the flow channel using the inertance L, a relation of $\Delta P = L \times dQ/dt$ is derived, where $\Delta P$ is the pressure difference of the flow channel and Q is the flow rate of the fluid flowing in the flow channel.

In other words, the inertance L shows a degree of influence applied to the change of flow rate with time and, the larger the inertance L, the smaller change of flow rate with time is resulted, while the smaller the inertance L, the larger change of flow rate with time is resulted.

Here, the synthetic inertance L1 on the side of the inlet flow channel 81 is calculated within a range of the inlet flow channel 81. In this case, since the tube 4 connecting the pump 10 and the inlet flow channel 81 has flexibility, it maybe excluded from the calculation of the synthetic inertance L1.

As regards the synthetic inertance L2 on the side of the outlet flow channel 82, since the flow channel diameter of the connecting flow channel 91 is significantly larger than that of the outlet flow channel 82 and the thickness of a tubular portion (tubular wall) of the connecting flow channel tube 90 is thin, the influence on the synthetic inertance L2 is negligible. Therefore, the synthetic inertance L2 on the side of the outlet flow channel 82 may be replaced by the inertance of the outlet flow channel 82.

The thickness of the tubular wall of the connecting flow channel tube 90 has a sufficient rigidity with respect to pressure propagation of the fluid.

In the first embodiment, the length and the cross-sectional area of the inlet flow channel 81 and the length and the cross-sectional area of the outlet flow channel 82 are set so that the synthetic inertance L1 on the side of the inlet flow channel 81 becomes larger than the synthetic inertance L2 on the side of the outlet flow channel 82.

Subsequently, the fluid discharging operation will be described.

The liquid is supplied to the inlet flow channel 81 by the pump 10 always at a constant pressure. Consequently, when no operation is performed by the piezoelectric element 30, the liquid flows into the fluid chamber 80 by the difference between a discharging force of the pump 10 and the flow channel resistance of the entire portion on the side of the inlet flow channel.

Assuming here that an operation signal is supplied to the piezoelectric element 30 and the piezoelectric element 30 is elongated abruptly in the vertical direction with respect to the surface of the diaphragm 40 on the side of the fluid chamber 80, the volume of the fluid chamber 80 is reduced and, if the synthetic inertances L1 and L2 on the side of the inlet flow channel and the outlet flow channel have sufficient magnitudes, the pressure in the fluid chamber 80 increases quickly and reaches several tens atmospheres.

This pressure is significantly larger than the pressure applied to the inlet flow channel 81 by the pump 10, flowing of the liquid from the inlet flow channel 81 into the fluid chamber 80 is reduced by this pressure, so that flowing out from the outlet flow channel 82 is increased.

Furthermore, since the synthetic inertance L1 on the side of the inlet flow channel is larger than the synthetic inertance L2 on the side of the outlet flow channel, the amount of reduction of the flow rate flowing from the inlet flow channel 81 into the fluid chamber 80 is smaller than the amount of increase of the liquid discharged from the outlet flow channel 82, and hence the discharge of the pulsed liquid, that is, the pulsating flow is generated in the connecting flow channel 91. The variations in pressure in the event of discharge is propagated in the connecting flow channel tube 90 (the connecting flow channel 91), and the fluid is injected from the fluid injection opening 96 of the nozzle 95 at the distal end.

Here, since the flow channel diameter of the fluid injection opening 96 is reduced in comparison with the flow channel diameter of the outlet flow channel 82, the liquid is further increased in pressure, and is injected at a high speed in the form of pulsed liquid drops.

In contrast, the interior of the fluid chamber 80 is brought into a vacuum state immediately after increase in pressure due to the interplay of reduction of the amount of the liquid flowing inward from the inlet flow channel 81 and increase in the amount of the liquid flowing outward from the outlet flow channel 82. Then, when the piezoelectric element 30 is restored to its original shape, the flow of the liquid in the inlet flow channel 81 toward the interior of the fluid chamber 80 at the similar velocity to the one before the operation (elongation) of the piezoelectric element 30 is restored after the elapse of a certain time due to both the pressure of the pump 10 and the vacuum state in the interior of the fluid chamber 80.

If the piezoelectric element 30 is elongated after having restored the flow of the liquid in the inlet flow channel 81, the pulsed liquid drops are continuously injected from the fluid injection opening 96.

Subsequently, a liquid discharging action from the discharge flow channel 83 will be described with reference to FIG. 2. First of all, a synthetic inertance L3 on the side of the discharge flow channel 83 will be described. Since the tube 5 has flexibility, the synthetic inertance L3 may be considered to be the sum of the inertances of the discharge flow channel 83 and the flow channel of the opening and closing valve 100. Then, the synthetic inertance L3 on the side of the discharge flow channel is set to be significantly smaller than the synthetic inertance L2 on the side of the outlet flow channel.

Therefore, when the opening and closing valve 100 is opened, the liquid is apt to flow to the side of the discharge flow channel 83 because of the relation between the synthetic inertance L3 and the synthetic inertance L2, so that flowing out from the outlet flow channel 82 may be restrained.

As the volume changing unit, the unit having a high response to expansion and contraction such as a piston can be used instead of the structure using the piezoelectric element 30 and the diaphragm 40.

Method of Controlling in First Embodiment

Subsequently, a method of controlling the pulsating flow generating apparatus according to the first embodiment will be described with reference to the drawings.

Figure 3:
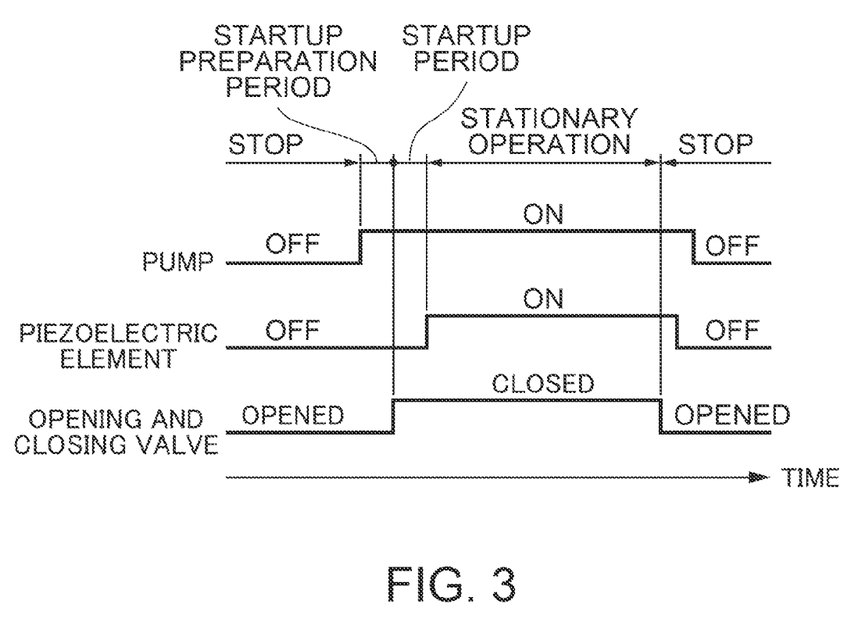
FIG. 3 is a timing chart showing a flow of a method of controlling the pulsating flow generating apparatus according to the first embodiment.
Figure 4:
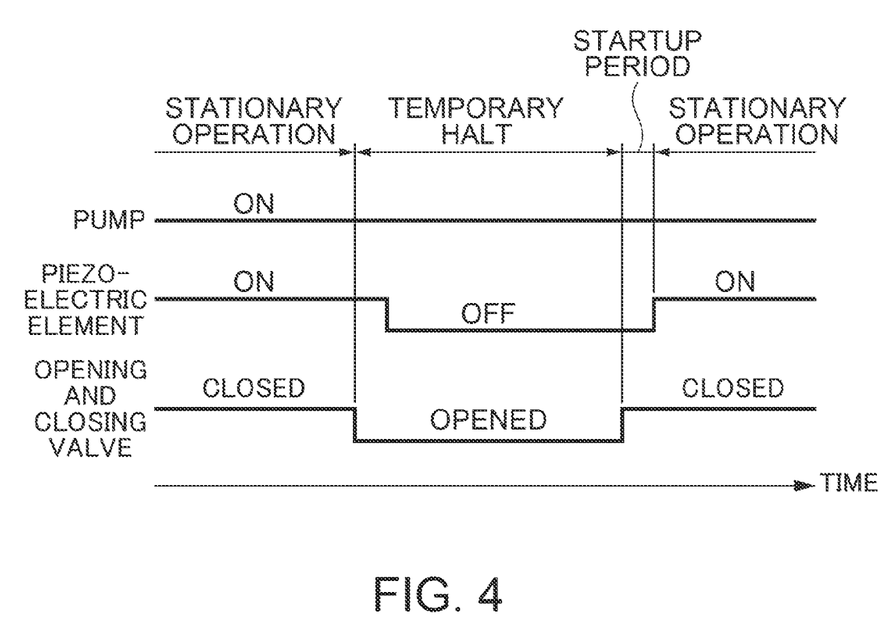
FIG. 4 is a timing chart showing a flow of a method of controlling the pulsating flow generating apparatus according to the first embodiment (a case where a temporary halt period is included).

FIG. 3 and FIG. 4 are timing charts showing flows of the method of controlling the pulsating flow generating apparatus in the first embodiment. FIG. 3 shows steps from the stop to the stationary operation of the pulsating flow generating apparatus, and FIG. 4 shows steps in a case of changing the state from the stationary operation to the temporary halt and then to the restart of the operation.

In FIG. 3, in the stop period of the pulsating flow generating apparatus 20, the pump 10 and the piezoelectric element 30 are stopped (turned OFF), and the opening and closing valve 100 is remained to be opened. Then, the pump 10 is operated by operating (turning ON) an external operating member 25 such as a switch provided on the pulsating flow generating apparatus 20 (first step).

This period is a startup preparation period of the pulsating flow generating apparatus 20 for starting the supply of the liquid into the fluid chamber 80, whereby the liquid can be stably supplied to the fluid chamber 80 at a flow rate per predetermined unit time. Then, since the opening and closing valve 100 is opened in this period, the supplied liquid is discharged outward from the discharge flow channel 83, so that the liquid is restrained from flowing out from the fluid injection opening 96.

In the startup preparation period of the pulsating flow generating apparatus 20, even though the supplied liquid is injected from the fluid injection opening 96, the flow rate of the injected liquid is not sufficient for incising or ablating the anatomy and only the liquid unnecessary for the incision or ablation of the anatomy is flowed out. When the liquid unnecessary for the incision or the ablation of the anatomy is injected from the fluid injection opening 96, the liquid may be bubbled after having landed on the anatomy, and exacerbate the visibility of the field of operation at the portion to be incised or ablated. Accordingly, in the first embodiment, in the startup preparation period of the pulsating flow generating apparatus 20, the exacerbation of the visibility of the field of operation is reduced by restraining the liquid from flowing out from the fluid injection opening 96 by opening the opening and closing valve 100.

Subsequently, the opening and closing valve 100 is closed (second step). The second step is a startup period of the pulsating flow generating apparatus 20 in which the opening and closing valve 100 is closed while operating the pump 10. This period is a period for closing the opening and closing valve 100 before starting the operation of the piezoelectric element 30, and increasing the pressure in the fluid chamber 80 to a pressure required for injecting the fluid.

Subsequently, the procedure goes to a third step for operating the piezoelectric element 30. The third step is a period for the stationary operation of the pulsating flow generating apparatus 20 and, in this period, the surgical operation is conducted. Since the piezoelectric element 30 is operated in a state in which the opening and closing valve 100 is closed in this period, the pressure in the fluid chamber 80 is sufficiently increased, and the liquid is injected in a pulsed manner at a high speed by the above-described operation of fluid injection.

When stopping the pulsating flow generating apparatus 20, the opening and closing valve 100 is opened and the pump 10 and the piezoelectric element 30 are stopped (fourth step). In this case, these operations may be performed substantially simultaneously. However, it is preferable to stop the piezoelectric element 30 and stop the pump 10 after a time lag from the opening of the opening and closing valve 100. Furthermore, it is preferable to open the opening and closing valve 100, stop the piezoelectric element 30, and then stop the pump 10 in this order.

The reason is that the order of these operations as described above contributes to avoid idling of the piezoelectric element 30 and prevent the piezoelectric element 30 from deteriorating due to excessive heating, and to restrain the tube 4 from expanding due to the liquid supply pressure from the pump 10 and the liquid from flowing out from the outlet flow channel 82 due to a restoring pressure of the tube 4.

Subsequently, another mode of the fourth step will be described. This is a step performed for changing the operating state from the stationary operation to the temporary halt and then to the restart of the operation, and description will be given with reference to FIG. 4. Here, the description will be given by replacing the fourth step with a fifth step. First of all, the pump 10 and the piezoelectric element 30 are operated (turned ON), the opening and closing valve 100 is opened from the stationary operation (third step) in which the opening and closing valve 100 is closed, and then the piezoelectric element 30 is stopped, while continuing the operation of the pump 10 (fifth step). Since the fifth step is the temporary halt period and hence the opening and closing valve 100 is opened, most part of the liquid to be supplied is discharged outward from the discharge flow channel 83. In the fifth step, the state is substantially the same as the state in the first step.

For restarting the operation, the procedure goes from the fifth step to the second step. In this case, since the pump 10 is continuously operated and supplies the liquid, the operation can be restarted immediately. For stopping, the opening and closing valve 100 is opened, and the procedure goes to the fourth step in which the pump 10 and the piezoelectric element 30 are stopped.

The operation and stopping (including the temporary halt and restart of the operation) of the pulsating flow generating apparatus 20 are performed by the external operating member 25 such as the switch provided on the pulsating flow generating apparatus 20, and the transition from the startup operation to the first step and then to the third step is performed by a program of the control unit, not shown.

According to the pulsating flow generating apparatus and the method of controlling the same in the first embodiment described above, the piezoelectric element 30 is kept in the state of not being operated, that is, the pulsating flow generating apparatus 20 is kept in the stopped state while opening the opening and closing valve 100. Then, since the synthetic inertance L3 of the discharge flow channel 83 is set to be smaller than the synthetic inertance L2 of the outlet flow channel 82, the liquid in the fluid chamber 80 is apt to flow toward the discharge flow channel 83 rather than toward the outlet flow channel 82. Therefore, in the state in which the pulsating flow generating apparatus 20 is stopped, the unnecessary liquid is restrained from flowing out from the fluid injection opening 96, so that the visibility of the field of operation at the portion to be incised or ablated is enhanced.

In addition, since the piezoelectric element 30 is operated in the state in which the opening and closing valve 100 is closed, the pressure in the fluid chamber 80 is sufficiently increased, and the liquid can be injected in a pulsed manner at a high speed.

Also, the tube 4, having flexibility, may be expanded due to the liquid supply pressure of the pump 10, and hence the liquid may be flowed into the fluid chamber 80 due to the restoring pressure of the tube 4 even when the pump 10 is stopped. Therefore, by opening the opening and closing valve 100, the liquid flows into the discharge flow channel 83, and hence the fluid may be restrained from flowing out from the fluid injection opening 96.

Also, in the startup preparation period of the pulsating flow generating apparatus 20 (first step), the state in which the liquid can be supplied into the fluid chamber 80 at the flow rate per predetermined unit time is achieved. In this period, since the opening and closing valve 100 is opened, the liquid is flowed to the discharge flow channel 83, and the liquid is prevented from flowing out from the fluid injection opening 96, so that the visibility of the field of operation at the portion to be incised or ablated is enhanced.

In the startup period of the pulsating flow generating apparatus (second step), the opening and closing valve 100 is closed while operating the pump 10. In this period, the opening and closing valve 100 is closed before starting the operation of the piezoelectric element 30, and the pressure in the fluid chamber 80 is increased to a pressure required for injecting the fluid. In this configuration, the liquid having energy sufficient for incising or ablating the anatomy can be injected in a pulsed manner at a high speed immediately after having started the operation of the piezoelectric element 30.

In the period of the stationary operation of the pulsating flow generating apparatus (third step), since the piezoelectric element 30 is operated in a state in which the opening and closing valve 100 is closed, the pressure in the fluid chamber 80 is sufficiently increased, and the liquid having energy sufficient for incising or ablating the anatomy can be injected in a pulsed manner at a high speed.

When stopping the pulsating flow generating apparatus 20, the pump 10 and the piezoelectric element 30 are stopped while opening the opening and closing valve 100 (fourth step). In this case, if the tube 4 is long or has flexibility, there may be a time difference from the stop of the operation of the pump 10 to the actual stop of the supply of the liquid. However, by setting the opening and closing valve 100 opened, the liquid is flowed to the discharge flow channel 83, and hence the fluid is prevented from flowing out from the fluid injection opening 96.

In the event of repeating "operation—temporary halt—restart of operation" in the operation of the pulsating flow generating apparatus 20, the operation of the pump 10 is continued in the state in which the opening and closing valve 100 is opened and the piezoelectric element 30 is stopped in the temporary halt period (fifth step). Therefore, since the liquid supply is continued, the time lag from the temporary halt to the restart of the operation can be reduced. Substantially, the temporary halt period and the startup preparation period are in the same state.

Second Embodiment

Subsequently, the pulsating flow generating apparatus according to a second embodiment will be described with reference to the drawings. In the second embodiment, the excessive liquid is forcedly discharged by disposing a sucking unit in the discharge flow channel 83 in contrast to the first embodiment described above in which the excessive liquid is discharged from the discharge flow channel 83 by using the synthetic inertance difference between the outlet flow channel 82 and the discharge flow channel 83. Therefore, parts common to those in the first embodiment are designated by the same reference numerals, and different portions are mainly described below.

Figure 5:
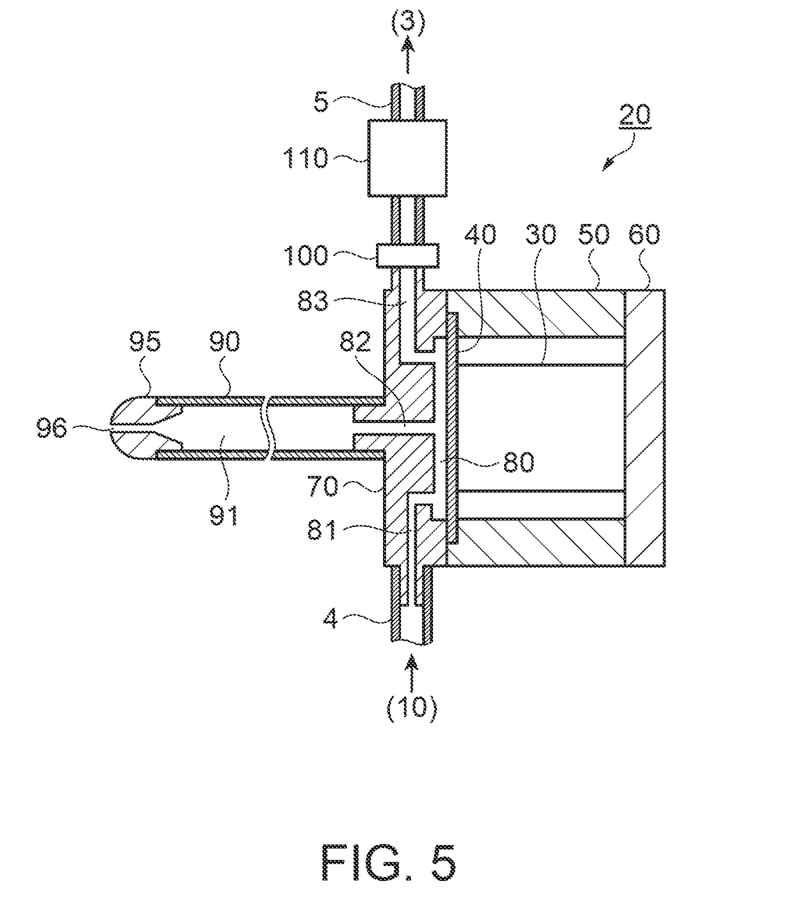
FIG. 5 is a cross-sectional view of the pulsating flow generating apparatus according to a second embodiment.

FIG. 5 is a cross-sectional view of the pulsating flow generating apparatus according to the second embodiment. In FIG. 5, a suction pump 110 as the sucking unit for sucking the liquid is disposed on the downstream side of the opening and closing valve 100 where the fluid is discharged, and is connected to the tube 5.

The suction pump 110 is operated and stopped substantially synchronous with opening and closing of the opening and closing valve 100. In other words, when opening the opening and closing valve 100, the suction pump 110 is operated to forcedly discharge the liquid in the fluid chamber 80 to the outside via the discharge flow channel 83. Then, when the opening and closing valve 100 is closed, the suction pump 110 is stopped.

Method of Controlling in Second Embodiment

Subsequently, a method of controlling the pulsating flow generating apparatus according to the second embodiment will be described with reference to the drawings.

Figure 6:
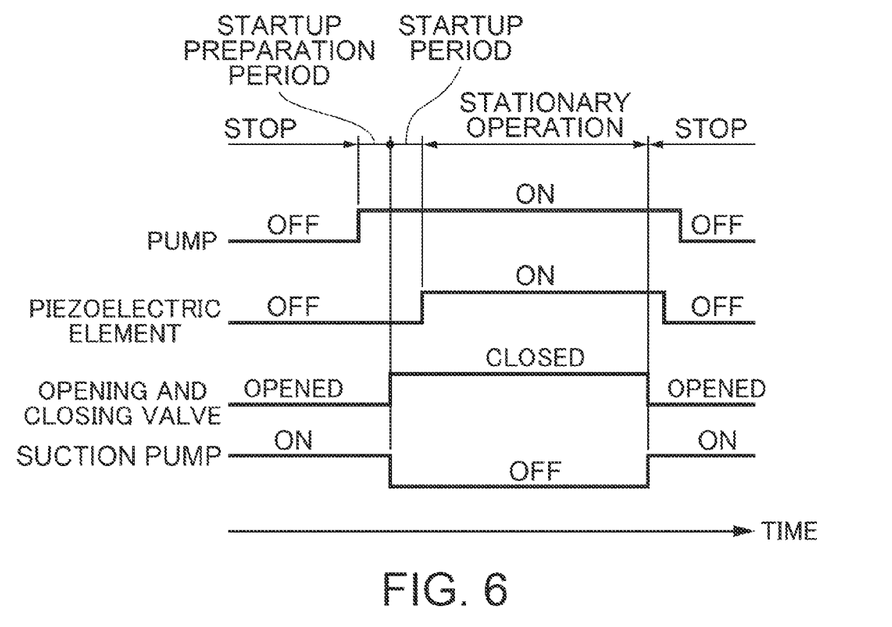
FIG. 6 is a timing chart showing a flow of a method of controlling the pulsating flow generating apparatus according to the second embodiment.
Figure 7:
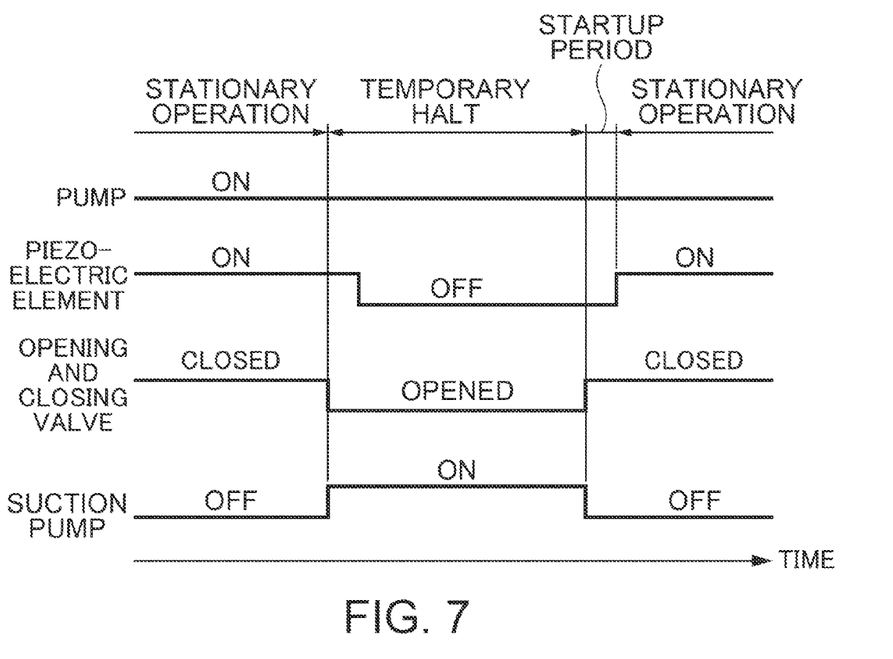
FIG. 7 is a timing chart showing a flow of a method of controlling the pulsating flow generating apparatus according to the second embodiment (a case where a temporary halt period is included).

FIG. 6 and FIG. 7 are timing charts showing flows of the method of controlling the pulsating flow generating apparatus in the second embodiment. FIG. 6 shows steps from the stop to the stationary operation of the pulsating flow generating apparatus, and FIG. 7 shows steps in a case of changing the state from the stationary operation to the temporary halt and then to the restart of the operation.

The operations of the pump 10, the piezoelectric element 30, and the opening and closing valve 100 are the same as in the first embodiment (see FIG. 3 and FIG. 4). Here, the timing of the operation of the suction pump 110 is substantially synchronous with the timing of opening and closing the opening and closing valve 100. Preferably, however, the timing of stopping the suction pump 110 is slightly advanced for the transition of the opening and closing valve 100 from the opened state to the closed state, and the timing of the operation of the suction pump 110 is slightly delayed for the transition of the opening and closing valve 100 from the closed state to the opened state.

In the case of temporary halt and the restart of the operation as well, the timing of the operation of the suction pump 110 is substantially synchronous with the opening and closing timing of the opening and closing valve 100.

According to the second embodiment, the same advantages as in the first embodiment described above are achieved. However, since the operation of the piezoelectric element 30 is stopped and the suction pump 110 is operated while opening the opening and closing valve 100 in this embodiment, the liquid in the fluid chamber 80 is forcedly discharged further reliably.

Also, since the suction pump 110 is provided in the discharge flow channel 83, the liquid is forcedly sucked even when the piezoelectric element 30 is operated in the temporary halt period, so that the flow out from the fluid injection opening 96 is restrained more reliably.

Furthermore, the time lag of the restart of the operation is reduced by the transition of the state from the temporary halt period to the first step (startup preparation period), the second step (startup period), and the third step (stationary operation period) in sequence.

Third Embodiment

Subsequently, the pulsating flow generating apparatus according to a third embodiment will be described with reference to the drawings. In the third embodiment, the discharge flow channel is communicated with the outlet flow channel in contrast to the first embodiment and the second embodiment described above in which the discharge flow channel is communicated directly with the fluid chamber. Parts common to those in the first embodiment are designated by the same reference numerals, and different portions are mainly described below.

Figure 8:
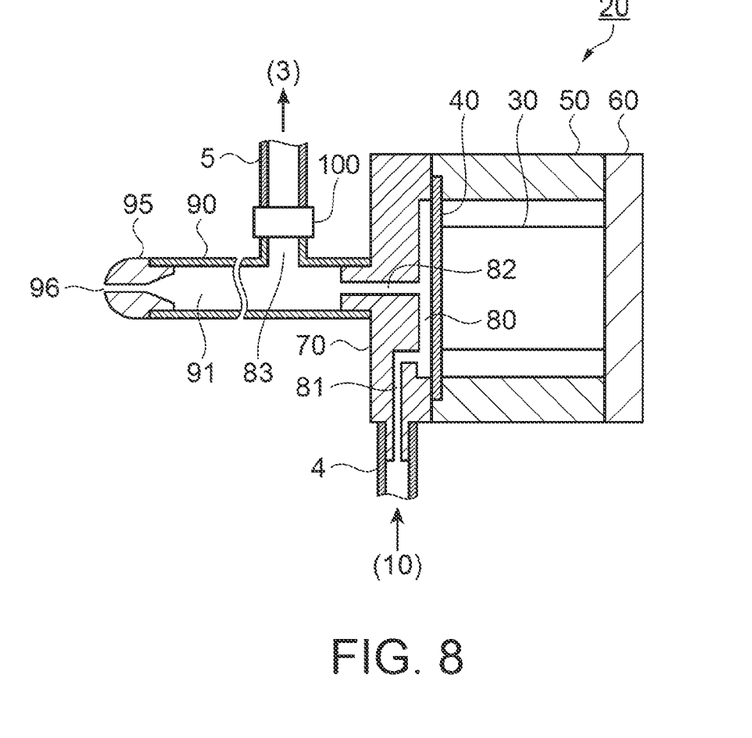
FIG. 8 is a cross-sectional view of the pulsating flow generating apparatus according to a third embodiment.

FIG. 8 is a cross-sectional view of the pulsating flow generating apparatus according to the third embodiment. In FIG. 8, the discharge flow channel 83 is connected so as to be communicated with the connecting flow channel 91 of the connecting flow channel tube 90. In the third embodiment, the connecting flow channel 91 is part of the outlet flow channel 82.

The discharge flow channel 83 is provided with the opening and closing valve 100. Here, the synthetic inertance L3 of the discharge flow channel 83 is set to be smaller than the synthetic inertance L2 of the outlet flow channel 82. The flow channel diameter of the fluid injection opening 96 is reduced in comparison with the flow channel diameter of the outlet flow channel 82. Therefore, when the opening and closing valve 100 is opened, the supplied liquid passes through the fluid chamber 80, the outlet flow channel 82, and the connecting flow channel 91, and is discharged outward from the discharge flow channel 83 which allows the liquid to flow easily by using the synthetic inertance difference and the fluid resistance at the fluid injection opening 96.

The discharge flow channel 83 may have a structure which communicates with a midsection of the outlet flow channel 82. In this case, the inertance difference between the synthetic inertance L3 of the discharge flow channel 83 and the synthetic inertance L2 of the outlet flow channel 82 can easily be increased.

A configuration having the suction pump 110 (see FIG. 5) on the downstream side of the opening and closing valve 100 is also applicable. By the provision of the suction pump 110, setting of the magnitude relation of the synthetic inertance of the discharge flow channel 83 and the synthetic inertance of the outlet flow channel 82 is no longer necessary, so that the constraint in terms of designs of the inlet flow channel 81 and the outlet flow channel 82 of the pulsating flow generating apparatus 20 may be eliminated, and the excessive liquid can be forcedly discharged.

Therefore, in the third embodiment, the same advantages as in the first embodiment and the second embodiment described above are achieved.

In the third embodiment, the discharge flow channel is configured to be communicated with the outlet flow channel. In this configuration, the connecting portion between the fluid chamber and the flow channel communicated directly with the fluid chamber can be eliminated, so that air bubbles to be built up in the connecting portion may be reduced.

The pulsating flow generating apparatus configured to generate a pulsating flow by changing the volume of the fluid chamber with the volume changing unit may not be able to generate the pulsating flow sufficient for incising or ablating the anatomy if the air bubbles exist in the fluid chamber because the internal pressure cannot be increased sufficiently. Therefore, with the structure in which the discharge flow channel 83 is brought into communication with the outlet flow channel 82 (connecting flow channel 91 in FIG. 8), air bubbles are restrained from building up in the fluid chamber 80, and the pressure in the fluid chamber 80 can advantageously be increased to a desired pressure.

Fourth Embodiment

Subsequently, the pulsating flow generating apparatus according to a fourth embodiment will be described with reference to the drawings. In the fourth embodiment, the pulsating flow generating apparatus is attached to a distal end of a tube and is configured to allow insertion into a canalicular organization such as a blood vessel in contrast to the first to the third embodiments described above in which the configuration of the pulsating flow generating apparatus operated by being held by the personal who conducts the surgical operation is exemplified.

Figure 9:
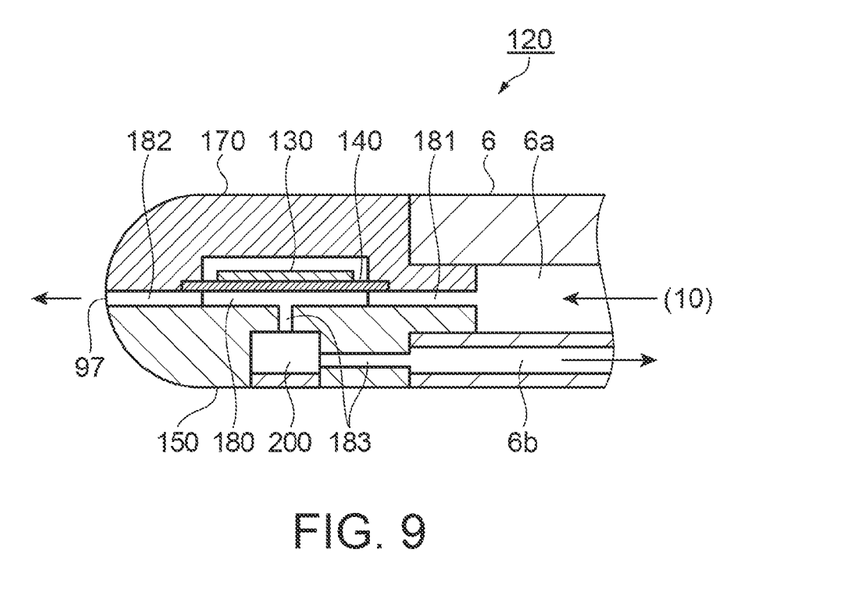
FIG. 9 is a cross-sectional view of the pulsating flow generating apparatus according to a fourth embodiment.

FIG. 9 is a cross-sectional view of the pulsating flow generating apparatus according to the fourth embodiment taken along the direction vertical to a diaphragm. A pulsating flow generating apparatus 120 is formed into a cylindrical shape having a substantially circular shape in cross-section in a state in which opposed surfaces of an upper case 170 and a lower case 150 are joined to each other. The surface of the lower case 150 opposing the upper case 170 is formed with a depression, and a fluid chamber 180 is defined by the depression and a diaphragm 140 tightly fixed to a surface of the upper case 170 opposing the lower case 150.

The lower case 150 is formed with an inlet flow channel 181 and an outlet flow channel 182 which communicate with the fluid chamber 180, and a piezoelectric element 130 is secured to the surface of the diaphragm 140 opposite from the fluid chamber 180.

A discharge flow channel 183 is formed on a bottom surface of the fluid chamber 180, and an opening and closing valve 200 is disposed at a midsection of the discharge flow channel 183.

The pulsating flow generating apparatus 120 configured in this manner is connected to a tube 6. The tube 6 includes a liquid supply connecting flow channel 6a communicated with the inlet flow channel 181 and a liquid discharging connecting flow channel 6b communicated with the discharge flow channel 183 opened therethrough.

The liquid supply connecting flow channel 6a is connected to the pump 10 (see FIG. 1), and the liquid discharging connecting flow channel 6b is connected to the suction pump 110 (see FIG. 5). Here, the pulsating flow generating apparatus 120 is an apparatus suitable for being inserted into the canalicular organization such as a blood vessel and removing attachment or the like in the canalicular organization, and has an outer diameter on the order of 2 mm to 5 mm. Therefore, the outer diameter of the tube 6 is substantially equal to the outer diameter of the pulsating flow generating apparatus 120. From these reasons, the tube 6 may be considered to be a catheter having the liquid supply connecting flow channel 6a and the liquid discharging connecting flow channel 6b.

The connecting surfaces between the tube 6 and the pulsating flow generating apparatus 120 are tightly adhered by sealing agent, so that the structure free from leakage of liquid is achieved.

Then, since the length of the tube 6 is from 1000 mm to 1500 mm, the pump 10 and the suction pump 110 are provided at positions apart from the pulsating flow generating apparatus 120 by 1000 mm to 1500 mm. The liquid supply connecting flow channel 6a and the liquid discharging connecting flow channel 6b are branched by a branching apparatus (not shown) in the vicinity of the pump 10 or the suction pump 110.

A fluid injecting action in the fourth embodiment is achieved by the same control method as in the first embodiment described above. A discharging action for discharging unnecessary liquid is achieved by the control method in the second embodiment described above.

The suction pump 110 can be omitted by setting the synthetic inertance L3 of the discharge flow channel 183 to be smaller than the synthetic inertance L2 of the outlet flow channel 182.

Even with the pulsating flow generating apparatus formed into a thin cylindrical shape configured in this manner, the same advantages as in the first to the third embodiments described above are achieved, and the invention is effective as a surgical equipment suitable for being inserted into the canalicular organization and removing attachment on an inner wall thereof.

In addition, the pulsating flow generating apparatus can be used for washing the interior of the tube of the canalicular structure.

What is claimed is:

1. A pulsating flow generating apparatus comprising:
    a fluid chamber which is configured to contains a fluid;
    an inlet flow channel for supplying fluid from a fluid supplying unit to the fluid chamber;
    a volume changing unit that changes the volume of the fluid chamber;
    an outlet flow channel connected to the fluid chamber and a fluid injection opening and which that delivers the fluid from the fluid chamber to the fluid injection opening;
    a discharge flow channel connected to the fluid chamber at an area separate from the area where the outlet flow channel is connected to the fluid chamber, the discharge flow channel discharging the fluid from the fluid chamber; and
    an opening and closing valve that opens and closes the discharge flow channel, wherein
    the synthetic inertance of the discharge flow channel is set to be smaller than the synthetic inertance of the outlet flow channel,
    the synthetic inertance of the inlet flow channel is set to be larger than the synthetic inertance of the outlet flow channel,
    an operation of the volume changing unit is started while closing the opening and closing valve,
    the operation of the volume changing unit is stopped while opening the opening and closing valve, and
    the liquid discharged via the discharge flow channel is discharged outside of the pulsating flow generating apparatus.

2. The pulsating flow generating apparatus according to claim 1, wherein
    the operation of the volume changing unit is started after a time lag from the closing of the opening and closing valve, and
    the operation of the volume changing unit is stopped after a time lag from the opening of the opening and closing valve.

3. The pulsating flow generating apparatus according to claim 1, wherein
    the discharge flow channel is communicated with the outlet flow channel.

* * * * *